United States Patent [19]

Abbott et al.

[11] 4,304,716

[45] Dec. 8, 1981

[54] S 31794/F-1 NUCLEUS

[75] Inventors: Bernard J. Abbott, Greenwood; David S. Fukuda, Brownsburg, both of Ind.

[73] Assignee: Eli Lilly and Company, Indianapolis, Ind.

[21] Appl. No.: 181,036

[22] Filed: Aug. 25, 1980

Related U.S. Application Data

[63] Continuation-in-part of Ser. No. 103,313, Dec. 13, 1979, abandoned.

[51] Int. Cl.³ ...................... C07C 103/52; C12P 21/04
[52] U.S. Cl. ................................. 260/112.5 R; 435/71
[58] Field of Search ..................... 260/112.5 R; 435/71

[56] References Cited

U.S. PATENT DOCUMENTS

| | | | |
|---|---|---|---|
| 3,150,059 | 9/1964 | Kleinschmidt et al. | 260/112.5 R |
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgens et al. | 260/112.5 R |
| 4,050,989 | 9/1977 | Kuwana et al. | 260/112.5 R |
| 4,173,629 | 11/1979 | Dreyfuss et al. | 260/112.5 R |

FOREIGN PATENT DOCUMENTS

| | | | |
|---|---|---|---|
| 834289 | 8/1975 | Belgium | 260/112.5 R |
| 859067 | 2/1977 | Belgium | 260/112.5 R |
| 866095 | 4/1977 | Belgium | 260/112.5 R |
| 851310 | 8/1977 | Belgium | 260/112.5 R |
| 38-405867 | 7/1963 | Japan | 260/112.5 R |
| 568386 | 4/1972 | Switzerland | 260/112.5 R |

OTHER PUBLICATIONS

T. Kato, et al., J. Antibiotics 29, 1339–1340 1976.
S. Chihara, et al., Agr. Biol. Chem. 37(11) 2455–2463; 37(12), 2709–2717 (1973).
S. Chihara, et al., Ibid. 38(3), 521–529; 38(10), 1767–1777 (1974).
T. Suzuki, et al., J. Biochem. 56(4), 335–343 (1964).
J. M. Weber, et al., J. Antibiotics 31(4), 373–374 1978.
J. Shoji, et al., J. Antibiotics 28, 764–769, 1975.
J. Shoji, et al., Ibid. 29(4), 380–389; 29(12) 1268–1274, 1275–1280 (1976).
F. Benz, et al., Helv. Chim. Acta 57, 2459 1974.
C. Keller-Juslem, et al., Tetrahedron Letter 4147 (1976).
R. Traber, et al., Helv. Chim. Acta 62, 1979, 1252.

*Primary Examiner*—Delbert R. Phillips
*Attorney, Agent, or Firm*—Nancy J. Harrison; Arthur R. Whale

[57] ABSTRACT

S 31794/F-1 nucleus, which is prepared by enzymatic deacylation of antibiotic S 31794/F-1 using an enzyme produced by the Actinoplanaceae, preferably by *Actinoplanes utahensis*. S 31794/F-1 nucleus and salts thereof are useful intermediates for the preparation of new semi-synthetic antifungal agents.

16 Claims, No Drawings

S 31794/F-1 NUCLEUS

CROSS-REFERENCE TO RELATED APPLICATION

This application is a continuation-in-part of application Ser. No. 103,313, filed Dec. 13, 1979, now abandoned.

SUMMARY OF THE INVENTION

This invention relates to S 31794/F-1 nucleus of the formula:

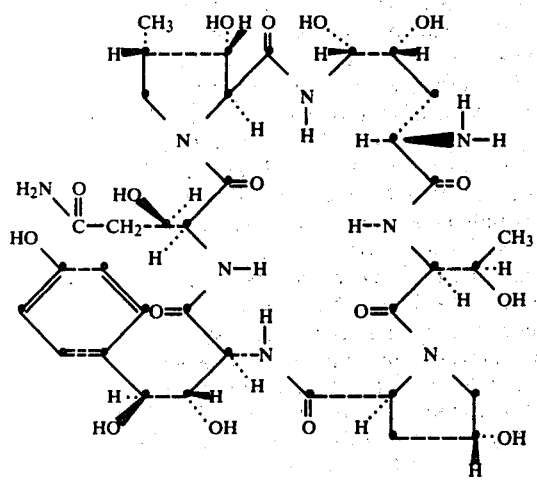

and acid-addition salts thereof. Throughout this application, the cyclic peptide formulas, such as formula 1, assume that the amino acids represented are in the L-configuration. S 31794/F-1 nucleus and its salts are useful as intermediates in the preparation of semi-synthetic antifungal agents.

In another aspect, this invention relates to a method of deacylating the cyclic peptide antibiotic S 31794/F-1. We have discovered a method of enzymatically removing the myristoyl side chain of S 31794/F-1 to give the cyclic peptide nucleus. For convenience herein, this nucleus will be called S 31794/F-1 nucleus. The method comprises exposing the antibiotic in an aqueous medium to an enzyme produced by a microorganism of the family Actinoplanaceae until substantial deacylation is accomplished.

A preferred method of this invention comprises using an enzyme produced by the microorganism *Actinoplanes utahensis* NRRL 12052 to cleave the fatty acid side chain. Deacylation is ordinarily accomplished by adding the antibiotic to a culture of *A. utahensis* and permitting the culture to incubate until deacylation is accomplished. The S31794/F-1 nucleus thereby obtained is separated from the fermentation broth by methods known in the art. This nucleus is useful in that it can be reacylated to provide new antibiotic substances.

DETAILED DESCRIPTION OF THE INVENTION

Field of the Invention

The S 31794/F-1 nucleus of this invention is obtained by deacylating the cyclic peptide antibiotic S 31794/F-1.

Antibiotic S 31794/F-1, which is disclosed in German Offenlegungsschrift No. 2,628,965 (Derwent Abstract 06057Y/04) and in U.S. Pat. No. 4,173,629, is an antifungal compound produced by *Acrophialophora limonispora* nov. spec. Dreyfuss et Muller NRRL 8095. S 31794/F-1 has the following characteristics: m.p. 178°–180° C. (dec.) (amorphous) or 181°–183° C. (dec.) (crystalline); $[\alpha]_D^{20} -24°$ (c 0.5, $CH_3OH$) or $+37°$ (c 0.5, methanol (crystalline); UV absorption maxima in methanol at 194 nm ($E_{1\,cm}^{1\%}=807$), 225 nm (shoulder) ($E_{1\,cm}^{1\%}=132$), 276 nm ($E_{1\,cm}^{1\%}=12.8$), 284 nm (shoulder) ($E_{1\,cm}^{1\%}=10.5$); $^{13}$C-NMR spectrum in deuteromethanol (190 mg in 1.5 ml deuteromethanol, tetramethylsilane as internal standard) with the following characteristics (crystalline):

| PPM | PPM | PPM |
|---|---|---|
| 176.2 | 75.5 | 51.2 |
| 175.0 | 74.0 | 39.7 |
| 173.7 | 71.0 | 38.8 |
| 172.6 | 70.5 | 36.6 |
| 172.0 | 69.7 | 34.8 |
| 171.8 | 68.0 | 32.8 |
| 171.7 | 62.2 | 30.6 |
| 168.6 | 58.3 | 26.7 |
| 157.7 | 57.0 | 23.5 |
| 132.5 | 56.2 | 19.7 |
| 129.0 | 55.4 | 14.3 |
| 115.9 | 52.9 | 11.1 |
| 76.6 | | | an approximate elemental analysis (after drying crystalline material for two hours in a high vacuum at 100° C.) as follows: 55.5–56.5 percent carbon, 7.5–7.7 percent hydrogen, 10.5–10.8 percent nitrogen and 25.5–26.0 percent oxygen. S 31794/F-1 is readily soluble in methanol, ethanol, pyridine, dimethyl sulfoxide and poorly soluble in water, chloroform, ethyl acetate, diethyl ether, benzene and hexane; and has antifungal activity, especially against *Candida albicans*.

Antibiotic S 31794/F-1 is believed to have structure 2.

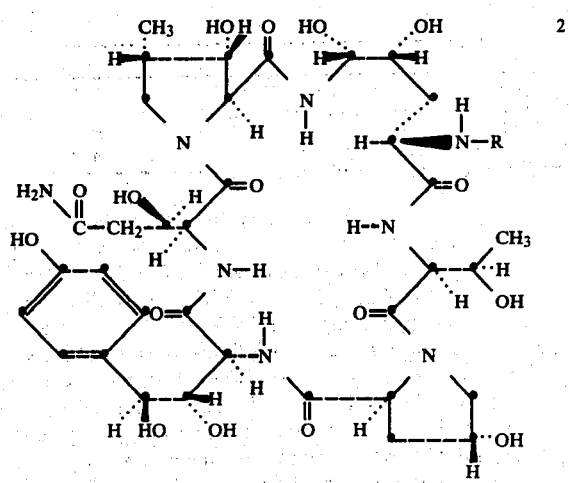

wherein R=myristoyl.

S 31794/F-1 Nucleus

The novel cyclic peptide nucleus of this invention, i.e., the nucleus of antibiotic S 31794/F-1 is believed to have the structure shown in formula 1.

S 31794/F-1 nucleus has an empirical formula of $C_{35}H_{52}N_8O_{16}$ and a molecular weight of 840.87.

Because the S 31794/F-1 nucleus contains an amino moiety, it may exist in the form of salts. Such salts are also useful as intermediates and for purification purposes. The pharmaceutically acceptable salts of the S 31794/F-1 nucleus are especially useful because purification of final products will be minimized. "Pharmaceutically acceptable" salts refer to those salts in which the toxicity of product as a whole toward warm-blooded animals is not increased.

Acid addition salts of S 31794/F-1 nucleus may be formed by standard reaction procedures with an inorganic or organic acid. Representative inorganic and organic acids include hydrochloric, hydrobromic, hydriodic, sulfuric, phosphoric, acetic, benzoic, sulfamic, tartaric, citric, maleic, succinic, ascorbic, glycolic, lactic, fumaric, palmitic, cholic, pamoic, mucic, D-glutamic, d-camphoric, glutaric, phthalic, lauric, stearic, salicylic, methanesulfonic, benzene-sulfonic, sorbic, picric, cinnamic, and other suitable acids.

PREPARATION of S 31794/F-1 Nucleus

A. Preparation of the Substrate

The S 31794/F-1 nucleus of this invention is prepared from antibiotic S 31794/F-1.

Antibiotic S 31794/F-1 is prepared by submerged aerobic cultivation of *Acrophialophora limonispora* NRRL 8095 as described in Example 2. This microorganism is a part of the permanent culture collection of the Northern Regional Research Center, U.S. Department of Agriculture, Agricultural Research Culture Collection, North Central Region, Peoria, Ill. 61604, from which it is available to the public under the designated NRRL number.

Antibiotic S 31794/F-1 has antifungal activity, particularly against Candida strains such as *Candida albicans*. Thus, production and isolation of the antibiotic can be monitored by bioautography using a Candida species such as *Candida albicans*.

S 31794/F-1 has the following $R_f$ values on silica-gel thin-layer chromatography (Merck, 0.25 mm):

| Solvent System | $R_f$ Value |
|---|---|
| Chloroform:methanol:water (71:25:4) | 0.17 |
| Chloroform:methanol:conc. acetic acid (70:29:1) | 0.19 |
| Chloroform:methanol (2:1) | 0.27 |

S 31794/F-1 can also be detected by iodine vapor.

As discussed in co-pending application Ser. No. 103,014 of Karl H. Michel entitled RECOVERY PROCESS FOR A-30912 ANTIBIOTICS, filed Dec. 13, 1979, reversed-phase high performance, low pressure liquid chromatography (HPLPLC) using silica gel/$C_{18}$ absorbent is a preferred method for the final purification of antibiotic S 31794/F-1. In this method (see Example 3), crude S 31794/F-1 [obtained, for example, by extracting the whole broth with ethyl acetate:isopropanol (4:1) and chromatographing the extract over silica gel and then over Sephadex] is dissolved in solvent and placed on a reversed-phase column equilibrated with the same solvent. The column is then eluted with the solvent. Fractions collected are monitored by *Candida albicans* bioautography and/or by UV (based on relative retention times). Fractions containing S 31794/F-1 are combined. It is sometimes necessary to carry out an additional chromatographic separation in order to obtain S 31794/F-1 in purified form.

B. Preparation of the Enzyme

1. The Producing Microorganism

The enzyme which is useful for deacylation of antibiotic S 31794/F-1 is produced by certain microorganisms of the family Actinoplanaceae, preferably the microorganism *Actinoplanes utahensis* NRRL 12052.

The enzyme may be the same enzyme which has been used to deacylate penicillins; this work is described by Walter J. Kleinschmidt, Walter E. Wright, Frederick W. Kavanagh, and William M. Stark in U.S. Pat. No. 3,150,059 (issued Sept. 22, 1964). Although a preferred method of cultivating *A. utahensis* NRRL 12052 to produce this enzyme is described in Example 1, it will be recognized by those skilled in the art that other methods may be used.

The Actinoplanaceae are a comparatively recent family of microorganisms of the order Actinomycetales. First described by Dr. John N. Couch, this family was established in 1955 [*J. Elisha Mitchell Sci. Soc.* 71, 148-155 (1955)]. The characteristics of the family and of many individual genera are found in "Bergey's Manual of Determinative Bacteriology", 8th ed., R. E. Buchanan and N. E. Gibbons, Eds., The Williams & Wilkins Co., Baltimore, Md., 1974, pages 706-723. Ten genera have thus far been distinguished: I. Actinoplanes (the type genus and thus far the most common genus); II. Spirillospora; III. Streptosporangium; IV. Amorphosporangium; V. Ampullariella; VI. Pilimelia; VII. Planomonospora; VIII. Planobispora; IX. Dactylosporangium; and X. Kitasatoa.

Some of the species and varieties which have been isolated and characterized so far are: *Actinoplanes philippinensis, Actinoplanes armeniacus, Actinoplanes utahensis,* and *Actinoplanes missouriensis; Spirillospora albida; Streptosporiangium roseum, Streptosporangium vulgare, Streptosporangium roseum* var. *hollandensis, Streptosporangium album, Streptosporangium viridialbum, Amorphosphorangium auranticolor, Ampullariella regularis, Ampullariella campanulata, Ampullariella lobata, Ampullariella digitata, Pilimelia terevasa, Pilimelia anulata, Planomonospora parontospora, Planomonospora venezuelensis, Planobispora longispora, Planobispora rosea, Dactylosporangium aurantiacum,* and *Dactylosporangium thailandense.*

The genus Actinoplanes is a preferred source of the enzyme which is useful for this invention. Within the genus Actinoplanes, the species *Actinoplanes utahensis* is an especially preferred source of the enzyme.

Cultures of representative species are available to the public from the Northern Regional Research Center, address supra, under the following accession numbers:

| | | |
|---|---|---|
| *Actinoplanes utahensis* | NRRL | 12052 |
| *Actinoplanes missouriensis* | NRRL | 12053 |
| *Actinoplanes* sp. | NRRL | 8122 |
| *Actinoplanes* sp. | NRRL | 12065 |
| *Streptosporangium roseum* var. *hollandensis* | NRRL | 12064 |

*A. utahensis* NRRL 12052 was derived from a parent culture which was deposited with the American Type Culture Collection (ATCC), 12301 Parklawn Drive, Rockville, Md. 20852 (*A. utahensis* ATCC 14539). The *A. utahensis* ATCC 14539 culture may also be used as a source of the enzyme.

*A. missouriensis* NRRL 12053 was derived from a culture which was also deposited with ATCC (*A. mis-*

*souriensis* ATCC 14538) and which is another source of the enzyme.

The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. Antibiotic S 31794/F-1 is then added to the culture. The pH of the fermentation medium is maintained at about pH 6.5. The culture is monitored for activity using a *Candida albicans* assay. This procedure is described in Sect. E. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. myristoyl) to restore activity.

2. Conditions for Enzyme Production

Production of the enzyme occurs under conditions satisfactory for growth of the Actinoplanaceae, i.e., a temperature between about 25 and about 30° C. and a pH of between about 5.0 and about 8.0, with agitation and aeration. The culture medium should contain (a) an assimilable carbon source such as sucrose, glucose, glycerol, or the like; (b) a nitrogen source such as peptone, urea, ammonium sulfate, or the like; (c) a phosphate source such as a soluble phosphate salt; and (d) inorganic salts found generally to be effective in promoting the growth of microorganisms. An effective amount of the enzyme is generally obtained in from about 40 to about 60 hours after the beginning of the growth cycle and persists for some time after the effective growth has been reached. The amount of enzyme produced varies from species to species of the organism and in response to different growth conditions.

As will be apparent to those in the field, the microorganisms, such as *Actinoplanes utahensis* NRRL 12052, which produce the enzyme are subject to variation. For example, artificial variants and mutants of these strains may be obtained by treatment with various known mutagens such as ultraviolet rays, X-rays, high-frequency waves, radioactive rays, and chemicals. All natural and artificial variants and mutants which are obtained from the Actinoplanaceae and which produce the enzyme may be used in this invention.

C. Deacylation Conditions

The substrate S 31794/F-1 is preferably added to the culture of Actinoplanaceae after the culture has been incubated for at least about 48 hours. The concentration of substrate in the conversion medium can vary widely. For maximum use of the enzyme and for substantially complete deacylation within a 24-hour period, however, the concentration of substrate will generally range from about 0.5 to about 1.0 mg/ml. Lower concentrations can be used, but may not make maximum use of the enzyme; higher concentrations can also be used, but the substrate may not be completely deacylated unless the fermentation time is extended.

Conversion of the substrate antibiotic to S 31794/F-1 nucleus according to this invention proceeds best when the pH of the fermentation medium is maintained in the range of from about 6.0 to about 7.0. A pH of about 6.5 is preferred.

After addition of the substrate, incubation of the culture should be continued for about 24 hours or longer. The purity of the substrate will affect the rate of deacylation. In general, when substrates of lower purity are used, the deacylation proceeds at a slower rate.

Multiple substrate feedings may be made. For example, 0.3–0.5 mg/ml of antibiotic may be fed at 12-hour intervals for at least five additions.

The deacylation can be carried out over a broad temperature range, e.g. from about 20° to about 45° C. It is preferable, however, to carry out the deacylation at temperatures of from about 25 to about 30° C. for optimum deacylation and stability of substrate and nucleus.

D. The Substrate

Purified antibiotic is a preferred substrate. Antibiotic S 31794/F-1 has antifungal, but no antibacterial, activity. Thus, the substrate materials may harbor bacterial cells or spores which could grow in the deacylation fermentation medium. Such contaminants can affect the deacylation reaction or the stability of the starting antibiotic or the product nucleus. It is important, therefore, that the substrates be sterile. Since autoclaving destroys most of the substrate antibiotic, it is preferable to sterilize preparations with ethylene oxide treatment in a pressurized system.

E. Monitoring the Deacylation

The starting material is an antifungal antibiotic which is especially active against *Candida albicans*. For this reason an assay using *C. albicans* is preferable for determining quantities of substrate present. The S 31794/F-1 nucleus which is formed is water soluble, but is biologically inactive. Reduction in biological activity is, therefore, a quick, presumptive test for deacylation. Both broth samples and alcoholic extracts of the fermentation solids should be assayed because the substrate is only slightly soluble in the broth.

F. Use of Resting Cells

An alternate method of deacylation involves removing the Actinoplanaceae cells from the culture medium, resuspending the cells in a buffer solution, and carrying out the deacylation as described in Sect. C. When this method is used, the enzymatically active mycelia can be re-used. For example, *A. utahensis* NRRL 12052 mycelia retain deacylase activity after storage for one month or longer under refrigeration (4°–8° C.) or in the frozen state (−20° C.). A preferred buffer solution is 0.1 molar phosphate buffer.

G. Immobilized Enzymes

Yet another method of carrying out the deacylation is to immobilize the enzyme by methods known in the art. (See, for example, "Biomedical Applications of Immobilized Enzymes and Proteins", Thomas Ming Swi Chang, Ed., Plenum Press, New York, 1977; Vol. 1.) The immobilized enzyme can then be used in a column (or other suitable type of reactor) to effect the deacylation.

In addition, the microorganism itself can be immobilized and used to catalyze the deacylation reaction.

UTILITY OF THE S 31794/F-1 NUCLEUS

The S 31794/F-1 nucleus and its acid-addition salts are useful intermediates in the preparation of synthetic antifungal compounds. Useful antifungal compounds prepared from S 31794/F-1 nucleus are described in a co-pending application of Bernard J. Abbott and David S. Fukuda (Docket No. X-5339, Ser. No. 103,130) and in two co-pending applications of Manuel Debono (Docket No. X-5595, Ser. No. 103,148, and Docket No. X-5398, Ser. No. 103,150) all of which are entitled DERIVATIVES OF S 31794/F-1 NUCLEUS and which were filed Dec. 13, 1979. Continuation-in-part applications of these applications, with the corresponding Docket Nos. X-5339A, Ser. No. 181,445 X-5595A, Ser. No. 181,436 and X-5398A, Ser. No. 181,037 are being filed herewith this even date.

The compounds described in the Abbott and Fukuda application have the general formula shown in structure 3:

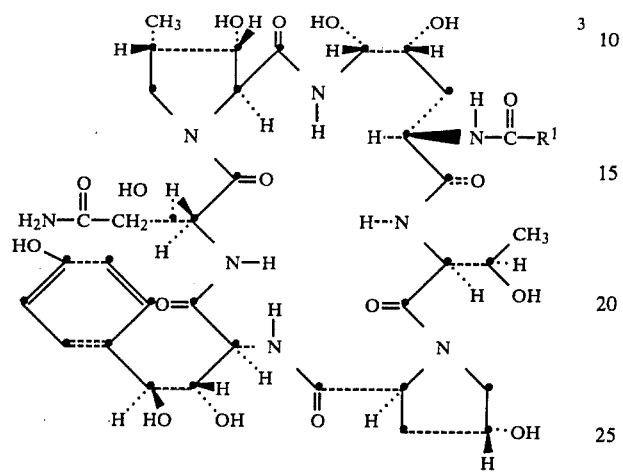

wherein $R^1$ is $C_6$–$C_{24}$ alkyl or $C_6$–$C_{24}$ alkenyl; provided that, when $R^1$ is alkyl, it cannot be n-tridecyl.

The term "alkyl" means a univalent, saturated, straight-chain or branched-chain hydrocarbon radical. The term "alkenyl" means a univalent, unsaturated, straight-chain or branched-chain hydrocarbon radical containing not more than three double bonds. The double bonds of the unsaturated hydrocarbon chain may be either in the cis or trans configuration. By "$C_6$–$C_{24}$" is meant a hydrocarbon (including straight and branched chains) containing from 6 to 24 carbon atoms.

The following are preferred embodiments of the compounds of formula 3:

(a) compounds wherein $R^1$ is alkyl of the formula $CH_3(CH_2)_n$—, wherein n is an integer from 5 to 23, provided that n cannot be 12, 13, 14, or 16;

(b) compounds wherein $R^1$ is alkyl of the formula $CH_3(CH_2)_n$—, wherein n is 10, 11, 15, 17, 18, 19, or 20;

(c) compounds wherein $R^1$ is alkyl of the formula

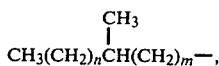

wherein n and m are each independently an integer from 0 to 21 provided that n+m must be no less than 3 and no greater than 21;

(d) compounds wherein $R^1$ is alkenyl containing one cis or trans double bond;

(e) compounds wherein $R^1$ is cis or trans alkenyl of the formula $$CH_3(CH_2)_nCH=CH(CH_2)_m—$$

wherein n and m are each independently an integer from 0 to 21, provided that n+m must be no less than 3 and no greater than 21;

(f) compounds wherein $R^1$ is alkenyl contaning two cis or trans double bond;

(g) compounds wherein $R^1$ is cis or trans alkenyl of the formula

wherein n and p are each, independently, an integer of from 0 to 18 and m is an integer of from 1 to 19, provided that m+n+p must be no less than 1 and no greater than 19 and that $R^1$ cannot be linoleoyl; and (h) the compounds wherein $R^1$ is:
cis,cis-8,11-heptadecadienyl
cis-$CH_3(CH_2)_5CH=CH(CH_2)_7$—
trans-$CH_3(CH_2)_5CH=CH(CH_2)_7$—
cis-$CH_3(CH_2)_{10}CH=CH(CH_2)_4$—
trans-$CH_3(CH_2)_{10}CH=CH(CH_2)_4$—
cis-$CH_3(CH_2)_7CH=CH(CH_2)_7$—
trans-$CH_3(CH_2)_7CH=CH(CH_2)_7$—
cis-$CH_3(CH_2)_5CH=CH(CH_2)_9$—
trans-$CH_3(CH_2)_5CH=CH(CH_2)_9$—
cis-$CH_3(CH_2)_7CH=CH(CH_2)_9$—
trans-$CH_3(CH_2)_7CH=CH(CH_2)_9$—
cis-$CH_3(CH_2)_7CH=CH(CH_2)_{11}$—
trans-$CH_3(CH_2)_7CH=CH(CH_2)_{11}$—
trans,trans-$CH_3(CH_2)_4CH=CHCH_2CH=CH(CH_2)_7$—
cis,cis,cis-$CH_3CH_2CH=CHCH_2CH=CHCH_2CH=CH—(CH_2)_7$—
n-tetradecyl
n-heptadecyl.

THE DEBONO DERIVATIVES

The compounds of the two Debono applications have the chemical structure depicted in formula 4:

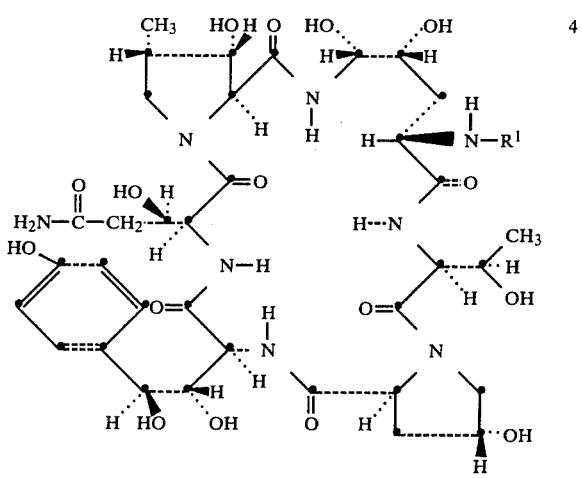

A. Debono Group I

In the group of derivatives described in Debono application Ser. No. 103,148, Docket No. X-5595 (Debono Group I), $R^1$ is an N-alkanoyl amino acyl group of the formula

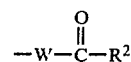

wherein:
W is a divalent aminoacyl radical of the formula:

 (a)

wherein A is $C_1$-$C_{10}$ alkylene or $C_5$-$C_6$ cycloalkylene;

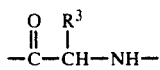 (b)

wherein $R^3$ is hydroxymethyl, hydroxyethyl, mercaptomethyl, mercaptoethyl, methylthioethyl, 2-thienyl, 3-indolemethyl, phenyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkylthio, carbamoyl, or $C_1$-$C_3$ alkylcarbamoyl;

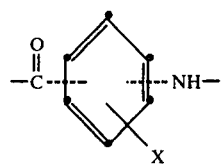 (c)

wherein X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamoyl, or $C_1$-$C_3$ alkylcarbamoyl;

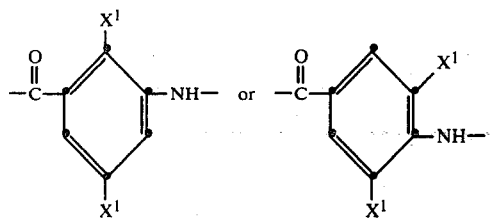 (d)

wherein $X^1$ is chloro, bromo, or iodo;

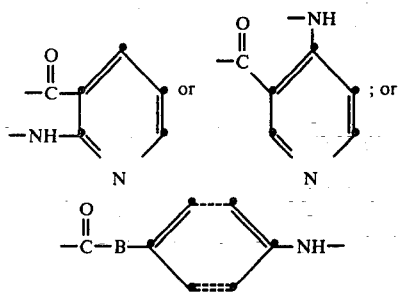 (e)

 (f)

wherein B is a divalent radical of the formula: —(CH$_2$)$_n$—, wherein n is an integer from 1 to 3; —CH=CH—; —CH=CH—CH$_2$—; or $$-\overset{O}{\underset{\|}{C}}NHCH_2-$$

and $R^2$ is $C_1$-$C_{17}$ alkyl or $C_2$-$C_{17}$ alkenyl.

The terms "alkylene", "alkyl", "alkoxy", "alkylthio", and "alkenyl" refer to both straight and branched hydrocarbon chains. "Alkyl" means a univalent saturated hydrocarbon radical. "Alkenyl" means a univalent unsaturated hydrocarbon radial containing one, two, or three double bonds, which may be oriented in the cis or trans configuration. "Alkylene" means a divalent saturated hydrocarbon radical. "Cycloalkylene" means a divalent cyclic saturated hydrocarbon radical.

Illustrative, preferred $C_1$-$C_{10}$ alkylene radicals are:
—CH$_2$—;

in which $R^5$ is $C_1$-$C_4$ alkyl (i.e., methyl, ethyl, n-propyl, isopropyl, n-butyl, tert-butyl, isobutyl, or 1-methylpropyl); —(CH$_2$)$_m$— in which m is an integer from 2 to 10, and

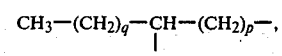

in which p is an integer from 1 to 8 and q is an integer from 0 to 7, provided that n+m must be no greater than 8.

Illustrative, preferred $C_1$-$C_{17}$ alkyl groups are:
(a) CH$_3$—;
(b) —(CH$_2$)$_n$CH$_3$ wherein n is an integer from 1 to 16; and
(c)

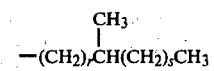

wherein r and s are independently an integer from 0 to 14 provided that r+s can be no greater than 14.

Ilustrative, preferred $C_2$-$C_{17}$ alkenyl radicals are:
(a) —(CH$_2$)$_t$—CH=CH—(CH$_2$)$_u$—CH$_3$ wherein t and u are independently an integer from 0 to 14 provided that t+u can be no greater than 14; and
(b) —(CH$_2$)$_v$—CH=CH—(CH$_2$)$_y$—CH=CH—(CH$_2$)$_z$—CH$_3$ wherein v and z are independently an integer from 0 to 11 and y is an integer from 1 to 12 provided that v+y+z can be no greater than 11.

In particular, the following $C_1$-$C_{17}$ alkyl groups are preferred:
CH$_3$—
CH$_3$(CH$_2$)$_5$—
CH$_3$(CH$_2$)$_6$—
CH$_3$(CH$_2$)$_8$—
CH$_3$(CH$_2$)$_{10}$—
CH$_3$(CH$_2$)$_{12}$—
CH$_3$(CH$_2$)$_{14}$—
CH$_3$(CH$_2$)$_{16}$—.

The following $C_2$-$C_{17}$ alkenyl groups are especially preferred:
cis-CH$_3$(CH$_2$)$_5$CH=CH(CH$_2$)$_7$—
trans-CH$_3$(CH$_2$)$_5$CH=CH(CH$_2$)$_7$—
cis-CH$_3$(CH$_2$)$_{10}$CH=CH(CH$_2$)$_4$—
trans-CH$_3$(CH$_2$)$_{10}$CH=CH(CH$_2$)$_4$—
cis-CH$_3$(CH$_2$)$_7$CH=CH(CH$_2$)$_7$—
trans-CH$_3$(CH$_2$)$_7$CH=CH(CH$_2$)$_7$—
cis-CH$_3$(CH$_2$)$_5$CH=CH(CH$_2$)$_9$—
trans-CH$_3$(CH$_2$)$_5$CH=CH(CH$_2$)$_9$—
cis,cis-CH$_3$(CH$_2$)$_4$CH=CHCH$_2$CH=CH(CH$_2$)$_7$—
trans,trans-CH$_3$(CH$_2$)$_4$CH=CHCH$_2$CH=CH(CH$_2$)$_7$— cis,cis,cis-
CH$_3$CH$_2$CH=CHCH$_2$CH=CHCH$_2$CH=CH—(CH$_2$)$_7$—.

When "W" is a divalent radical of the formula

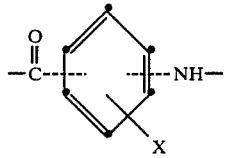

a preferred embodiment is that in which X is hydrogen and the

and —NH— functions are oriented in the para configuration.

The terms "substituted phenyl" and "substituted benzyl", as defined by R$^3$ in formula 4, contemplate substitution of a group at any of the available positions in the benzene ring—i.e. the substituent may be in the ortho, meta, or para configuration.

The term "C$_1$-C$_3$ alkyl", as defined by R$^3$ or X in formula 4, includes the methyl, ethyl, n-propyl, or isopropyl groups.

B. Debono Group II

In the group of derivatives of structure 4 described in Debono application Ser. No. 103,150, Docket No. X-5398 (Debono Group II), R$^1$ is a substituted benzoyl group of the formula 5:

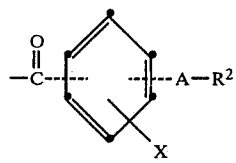

wherein A is divalent oxygen, sulfur, sulfinyl, or sulfonyl; X is hydrogen, chloro, bromo, iodo, nitro, C$_1$-C$_3$ alkyl, hydroxy, C$_1$-C$_3$ alkoxy, mercapto, C$_1$-C$_3$ alkylthio, carbamoyl, or C$_1$-C$_3$ alkylcarbamoyl; and R$^2$ is C$_5$-C$_{18}$ alkyl or C$_5$-C$_{18}$ alkenyl.

In the substituted benzoyl group (R$^1$), the

function and the —AR$^2$ function may be oriented on the benzene ring in the ortho, meta, or para position relative to each other. The para orientation is preferred. The substituent represented by X may be substituted at any available position of the benzene ring not occupied by the

and AR$^2$ groups.

The terms "alkyl" and "alkenyl" are as defined in the Group I derivatives.

Illustrative, preferred C$_5$-C$_{18}$ alkyl radicals are:
(a) —(CH$_2$)$_n$CH$_3$ wherein n is an integer from 4 to 17, and
(b)

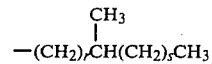

wherein r and s are, independently, an integer from 0 to 15, provided that r+s can be no greater than 15 or no less than 2.

Illustrative, preferred C$_5$-C$_{18}$ alkenyl radicals are:
(a) —(CH$_2$)$_t$—CH=CH—(CH$_2$)$_n$—CH$_3$ wherein t is an integer from 1 to 15, and n is an integer from 0 to 15 provided that t+n can be no greater than 15 or no less than 2; and
(b) —(CH$_2$)$_v$—CH=CH—(CH$_2$)$_y$—CH=CH—(CH$_2$)$_z$—CH$_3$ wherein v and z are, independently, an integer from 0 to 12 and y is an integer from 1 to 13 provided that v+y+z must be no greater than 13.

PREPARATION OF THE DERIVATIVES

The compounds of formulas 3 and 4 are prepared by acylating S 31794/F-1 nucleus at the α-amino group of the dihydroxyornithine portion of the nucleus with the appropriate acyl side chain using methods conventional in the art for forming an amide bond. The acylation is accomplished, in general, by reacting S 31794/F-1 nucleus with an activated derivative of the acid corresponding to the desired acyl side chain group.

The term "activated derivative" means a derivative which renders the carboxyl function of the acylating agent reactive to coupling with the primary amino group to form the amide bond which links the acyl side chain to the S 31794/F-1 nucleus. Suitable activated derivatives, their methods of preparation, and their methods of use as acylating agents for a primary amine will be recognized by those skilled in the art. Preferred activated derivatives are: (a) an acid halide (e.g. an acid chloride), (b) an acid anhydride (e.g. an alkoxyformic acid anhydride or aryloxyformic acid anhydride) or (c) an activated ester (e.g. a 2,4,5-trichlorophenyl ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of formulas 3 and 4 is by the active ester method. The use of the 2,4,5-trichlorophenyl ester of the desired acid as the acylating agent is most preferred. In this method, an excess amount of the active ester is reacted with S 31794/F-1 nucleus at room temperature in a non-reactive organic solvent such as dimethylformamide (DMF). The reaction time is not critical, although a time of about 15 to about 18 hours is preferred. At the conclusion of the reaction, the solvent is removed, and the residue is purified by a recognized method, such as by column chromatography. Chromatography using silica gel as the stationary phase and ethyl acetate:methanol (3:2) as the solvent system in a preferred method.

The 2,4,5-trichlorophenyl esters of the corresponding acids can be prepared conveniently by treating the desired acid with 2,4,5-trichlorophenol in the presence of a coupling agent, such as N,N'-dicyclohexylcarbodiimide. Other methods suitable for preparing acid esters will be apparent to those skilled in the art.

The alkanoic and alkenoic acids used as starting materials for the Abbott and Fukuda derivatives of formula 3 and the activated derivatives thereof (in particular, the acid chlorides and the 2,4,5-trichlorophenyl esters), are known compounds and can be prepared from known compounds by known methods. The 2,4,5-trichlorophenyl esters are conveniently made by treating the acid chloride of the alkanoic or alkenoic acid with 2,4,5-trichlorophenol in the presence of pyridine or by treating the free alkanoic or alkenoic acid with 2,4,5-trichlorophenol in the presence of N,N'-dicyclohexylcarbodiimide. The 2,4,5-trichlorophenyl ester derivative can be purified by column chromatography over silica gel in toluene.

The N-alkanoylamino acids or N-alkenoylamino acids used as starting materials for the Debono Group I derivatives of formula 4 are either known compounds or they can be made by acylating the appropriate amino acid with the appropriate alkanoyl or alkenoyl group using conventional methods. A preferred way of preparing the N-alkanoylamino acids is by treating the appropriate amino acid with an alkanoic acid chloride in pyridine. The alkanoic acids, the activated derivatives thereof, and the amino acids used are either known compounds or they can be made by known methods or by modification of known methods which will be apparent to those skilled in the art.

If a particular amino acid contains an acylable functional group other than the amino group, it will be understood by those skilled in the art that such a group must be protected prior to reaction of the amino acid with the reagent used to attach the N-alkanoyl or N-alkenoyl group. Suitable protecting groups can be any group known in the art to be useful for the protection of a side chain functional group in peptide synthesis. Such groups are well known, and the selection of a particular protecting group and its method of use will be readily known to one skilled in the art [see, for example, "Protective Groups In Organic Chemistry", M. McOmie, Editor, Plenum Press, New York, 1973].

It will be recognized that certain amino acids used in the synthesis of these products may exist in optically active forms. Both the natural configuration (L-configuration) and unnatural configuration (D-configuration) may be used as starting materials.

The substituted benzoic acids used as starting materials for the Debono II derivatives and the activated derivatives thereof are either known compounds or they can be made from known compounds by methods known in the art. The alkoxybenzoic acids or alkenyloxybenzoic acids can be prepared conveniently from an appropriate hydroxybenzoic acid by reacting an appropriate alkyl or alkenyl halide with the disodium salt of the appropriate hydroxybenzoic acid. The (alkylthio)benzoic acids or the (alkenylthio)benzoic acids can be prepared conveniently by treating the appropriate substituted S-(4-carbomethoxyphenyl)dimethylthiocarbamate of the general formula $CH_3CO_2C_6H_3X-S(CO)N(CH_3)_2$ with aqueous sodium hydroxide at 65°-85° C., then adding the appropriate alkyl or alkenyl bromide, and continuing heating for 2-4 hours. The substituted S-(4-carbomethoxyphenyl)dimethylthiocarbamates can be made from the appropriate hydroxybenzoic acids by the method of M. Newman and H. Kanes, J. Org. Chem. 31, 3980 (1966).

When it is desired to prepare a Debono II derivative of formula 4 wherein A is sulfinyl or sulfonyl, the appropriate sulfoxide or sulfone derivative of the (alkenylthio) or (alkylthio)benzoic acid (formula 5) can be used for acylation of the nucleus. The appropriate sulfoxides or sulfones can be made by oxidation of the corresponding thioether compound using conventional agents, such as m-chloroperbenzoic acid, tert-butyl hypochlorite, sodium metaperiodate, or hydrogen peroxide. If a double bond is present in the thioether, very mild conditions should be used to avoid epoxidation. If equimolar amounts of reactants are taken, the product is a sulfoxide (A is sulfinyl), which is readily oxidized to the sulfone (A is sulfonyl) by an additional mole of the oxidizing agent.

The hydroxybenzoic acids and substituted derivatives thereof used as starting materials in the processes described herein are either known compounds or can be prepared by conventional methods which are known in the art.

UTILITY OF THE DERIVATIVES

The compounds of formulas 3 and 4 inhibit the growth of pathogenic fungi and are useful, therefore, for controlling the growth of fungi on environmental surfaces (as an antiseptic) or in treating infections caused by fungi. In particular, the compounds are active against *Candida albicans* and are, thus, especially useful for treating candidosis. The activity of the compounds can be assessed in standard microbiological test procedures, such as in vitro in agar-plate disc-diffusion tests or in agar-dilution tests, or in vivo in tests in mice infected with *C. albicans*. The compounds are also active against *Trichophyton mentagrophytes* (a dermatophytic organism), *Saccharomyces pastorianus*, and *Neurospora crassa*.

When employed systemically, the dosage of the compounds of formulas 3 and 4 will vary according to the particular compound being employed, the severity and nature of the infection, and the physical conditions of the subject being treated. Therapy should be initiated at low dosages, the dosage being increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose, may be added to make the solutions isotonic. The proportions and nature of such additives will be apparent to those skilled in the art.

When used to treat vaginal Candida infections, the compounds of formulas 3 and 4 can be administered in combination with pharmaceutically acceptable conventional excipients suitable for intravaginal use. Formulations adapted for intravaginal administration will be known to those skilled in the art.

In order to illustrate the operation of this invention more fully, the following examples are provided.

EXAMPLE 1

Preparation of S 31794/F-1 Nucleus

A. Fermentation of *Actinoplanes utahensis*

A stock culture of *Actinoplanes utahensis* NRRL 12052 is prepared and maintained on an agar slant. The medium used to prepare the slant is selected from one of the following:

MEDIUM A

| Ingredient | Amount |
| --- | --- |
| Pre-cooked oatmeal | 60.0 g |
| Yeast | 2.5 g |
| $K_2HPO_4$ | 1.0 g |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.

*Czapek's mineral stock has the following composition:

| Ingredient | Amount |
| --- | --- |
| $FeSO_4 \cdot 7H_2O$ (dissolved in 2 ml conc HCl) | 2 g |
| KCl | 100 g |
| $MgSO_4 \cdot 7H_2O$ | 100 g |
| Deionized water | q.s. to 1 liter |

MEDIUM B

| Ingredient | Amount |
| --- | --- |
| Potato dextrin | 5.0 g |
| Yeast extract | 0.5 g |
| Enzymatic hydrolysate of casein* | 3.0 g |
| Beef extract | 0.5 g |
| Glucose | 12.5 g |
| Corn starch | 5.0 g |
| Meat peptone | 5.0 g |
| Blackstrap molasses | 2.5 g |
| $MgSO_4 \cdot 7H_2O$ | 0.25 g |
| $CaCO_3$ | 1.0 g |
| Czapek's mineral stock | 2.0 ml |
| Agar | 20.0 g |
| Deionized water | q.s. to 1 liter |

*N-Z-Amine A, Humko Sheffield Chemical, Lyndhurst, N.J.

The slant is inoculated with *Actinoplanes utahensis* NRRL 12052 and the inoculated slant is incubated at 30° C. for about 8 to 10 days. About ½ of the slant growth is used to inoculate 50 ml of a vegetative medium having the following composition:

| Ingredient | Amount |
| --- | --- |
| Pre-cooked oatmeal | 20.0 g |
| Sucrose | 20.0 g |
| Yeast | 2.5 g |
| Distiller's Dried Grain* | 5.0 g |
| $K_2HPO_4$ | 1.0 g |
| Czapek's mineral stock | 5.0 ml |
| Deionized water | q.s. to 1 liter | adjust to pH 7.4 with NaOH; after autoclaving, pH is about 6.8.

*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen", Cryobiol 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

MEDIUM I

| Ingredient | Amount (g/L) |
| --- | --- |
| Peanut meal | 10.0 |
| Soluble meat peptone | 5.0 |
| Sucrose | 20.0 |
| $KH_2PO_4$ | 0.5 |
| $K_2HPO_4$ | 1.2 |
| $MgSO_4 \cdot 7H_2O$ | 0.25 |
| Tap water | q.s. to 1 liter |

The pH of the medium is about 6.9 after sterilization by autoclaving at 121° C. for 45 minutes at about 16–18 psi.

MEDIUM II

| Ingredient | Amount (g/L) |
| --- | --- |
| Sucrose | 30.0 |
| Peptone | 5.0 |
| $K_2HPO_4$ | 1.0 |
| KCl | 0.5 |
| $MgSO_4 \cdot 7H_2O$ | 0.5 |
| $FeSO_4 \cdot 7H_2O$ | 0.002 |
| Deionized water | q.s. to 1 liter |

Adjust to pH 7.0 with HCl; after autoclaving, pH is about 7.0.

MEDIUM III

| Ingredient | Amount (g/L) |
| --- | --- |
| Glucose | 20.0 |
| $NH_4Cl$ | 3.0 |
| $Na_2SO_4$ | 2.0 |
| $ZnCl_2$ | 0.019 |
| $MgCl_2 \cdot 6H_2O$ | 0.304 |
| $FeCl_3 \cdot 6H_2O$ | 0.062 |
| $MnCl_2 \cdot 4H_2O$ | 0.035 |
| $CuCl_2 \cdot 2H_2O$ | 0.005 |
| $CaCO_3$ | 6.0 |
| $KH_2PO_4$* | 0.67 |
| Tap water | q.s. to 1 liter |

*Sterilized separately and added aseptically Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level above 30% of air saturation at atmospheric pressure.

B. Deacylation of Antibiotic S 31794/F-1

A fermentation of *A. utahensis* is carried out as described in Sect. A, using production medium I. After the culture is incubated for about 48 hours, antibiotic S 31794/F-1, dissolved in a small amount of methanol, is added to the fermentation medium.

Deacylation of S 31794/F-1 is monitored by paper-disc assay against *Candida albicans*. The fermentation is allowed to continue until deacylation is complete as indicated by disappearance of activity.

C. Isolation of S 31794/F-1 Nucleus

Whole fermentation broth, obtained as described in Sect. B is filtered. The mycelial cake is discarded. The clear filtrate thus obtained is passed through a column containing HP-20 resin (DIAION High Porous Polymer, HP-Series, Mitsubishi Chemical Industries Limited, Tokyo, Japan). The effluent thus obtained is discarded. The column is then washed with up to eight column volumes of deionized water at pH 6.5–7.5 to remove residual filtered broth. This wash water is discarded. The column is then eluted with a water:methanol (7:3) solution. Elution is monitored using the following procedure: Two aliquots are taken from each eluted fraction. One of the aliquots is concentrated to a small volume and is treated with an acid chloride such as myristoyl chloride, using the procedure described in Example 6. This product and the other (untreated) aliquot are assayed for activity against *Candida albicans*. If the untreated aliquot does not have activity and the acylated aliquot does have activity, the fraction contains S 31794/F-1 nucleus. The eluate containing S 31794/F-1 nucleus is concentrated under vacuum to a small volume and lyophilized to give crude nucleus.

D. Purification of S 31794/F-1 Nucleus by Reversed-Phase Liquid Chromatography

Crude S 31794/F-1 nucleus, obtained as described in Section C, is dissolved in water:acetonitrile:acetic acid:pyridine (96:2:1:1). This solution is chromatographed on a column filled with Lichroprep RP-18, particle size 25–40 microns (MC/B Manufacturing Chemists, Inc. E/M, Cincinnati, OH). The column is part of a Chromatospac Prep 100 unit (Jobin Yvon, 16-18 Rue du Canal 91160 Longjumeau, France). The column is operated at a pressure of 90–100 psi, giving a flow rate of about 60 ml/minute, using the same solvent. Separation is monitored at 280 nm using a UV monitor (ISCO Absorption Monitor Model UA-5, Instrumentation Specialties Co., 4700 Superior Ave., Lincoln, Neb. 68504) with an optical unit (ISCO Type 6).

On the basis of absorption at 280 nm, fractions containing S 31794/F-1 nucleus are combined, evaporated under vacuum and lyophilized to give purified S 31794/F-1 nucleus.

EXAMPLE 2

Preparation of Antibiotic S 31794/F-1

Antibiotic S 31794/F-1 is produced by submerged culture of *Acrophialophora limonispora* NRRL 8095 with stirring, shaking, and/or aeration at pH 3–8, preferably pH 5–7, and at 15°–30° C., preferably at 18°–27° C., for from 48 to 360 hours, preferably from 120 to 288 hours.

Antibiotic S 31794/F-1 is isolated by treating the culture broth (90 L) with ethyl acetate:isopropanol (4:1, 90 L) and homogenizing for 30 minutes at room temperature. The organic phase is separated and evaporated under vacuum at about 40° C. The residue thus obtained is chromatographed on a 10-fold amount of silica gel, using $CHCl_3:CH_3OH$ (95:5 to 60:40). Fractions which have antifungal activity are combined and chromatographed on a 100-fold amount of "Sephadex LH-20" with methanol. Fractions from the Sephadex column which have antifungal activity are combined and rechromatographed on a 100-fold amount of silica gel (0.05–0.2 mm) with a $CHCl_3:CH_3OH:H_2O$ (71:25:4) solvent system. The fractions eluted which have antifungal activity are combined and evaporated under vacuum to give crude antibiotic S 31794/F-1. This product is dissolved in small amounts of methanol and precipitated with diethyl ether to give S 31794/F-1 as a white amorphous powder, mp 178°–180° C. (dec.) after drying in high vacuum at 25°–30° C. Crystallization from a 10-fold amount of ethyl acetate:methanol:water (80:12:8) gives crystalline S 31794/F-1, mp 181°–183° C. (dec) after drying in high vacuum at 20° C.

EXAMPLE 3

Isolation of Antibiotic S 31794/F-1

Crude antibiotic S 31794/F-1, obtained as described in Example 2 after chromatography over Sephadex, is introduced onto a silica-gel column (Michel-Miller Column) through a loop with the aid of a valve system. The column is packed with LP-1/$C_{18}$ silica-gel reversed-phase resin (10-20 microns), prepared as described in Example 4, in chloroform:methanol:water (71:25:4) through a loop with the aid of a valve system. The slurry packing procedure described in Example 5 is used. The solvent is moved through the column using an F.M.I. pump with valveless piston design. Elution of the antibiotic is monitored using a UV monitor at 280 nm as in Example 1. Fractions having antifungal activity are combined and concentrated under vacuum to give antibiotic S 31794/F-1.

EXAMPLE 4

Preparation of Silica Gel/$C_{18}$ Reversed-Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16–20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16–20 hours).

EXAMPLE 5

Slurry Packing Procedure for Michel-Miller Columns

General Information

A. Analytical or preparative columns can be packed by this procedure.

B. Silica gels and silica gel reversed phase packings (e.g., Quantum LP-1, particle size 10–20 microns; Li-Chroprep RP-8 and RP-18, particle size 25–40 microns) are recommended. However, other silica gels (e.g., Shandons ODS Hypersil, particle size 5 microns) as well as other types of resins have been packed successfully by this procedure.

C. Generally, a pressure of less than 200 psi and flow rates between 5–40 ml/minute are required for this slurry packing technique; this is dependent on column volume and size. PLEASE NOTE: Packing pressure should exceed pressure used during actual separation by 30–50 psi; this will assure no further compression of the adsorbent during separation runs. Columns packed by this procedure with reversed-phase silica gel can be operated for several years without loss of efficiency.

D. Sudden decrease in pressure may cause cracks or channels to form in the packing material, which would greatly reduce column efficiency. Therefore, it is important to let the pressure drop slowly to zero whenever the pump has been turned off.

E. Approximate volume of columns (Ace Glass Cat. No., unpacked): 5795-04, 12 ml; 5795-10, 110 ml; 5795-16, 300 ml; 5795-24, 635 ml; and 5796-34, 34 ml.

F. The time required to pack a glass column will vary from minutes to several hours depending on column size and experience of the scientist.

EXAMPLE

1. Connect glass column to a reservoir column via coupling (volume of reservoir column should be twice that of the column). Place both columns in vertical positions (reservoir column above).

2. Weigh out packing material (ca. 100 g for 200 ml column).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant liquid.

5. Slurry the resin with sufficient solvent to fill reservoir column. Pour swiftly into reservoir. NOTE: The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).

7. Continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill precolumn with solvent and small amount of adsorbent; and pump at maximum pressure until column is completely packed. For additional information, see general procedure.

NOTE: Always allow pressure to decrease slowly after turning off pump—this will prevent formation of any cracks or channels in the packing material.

10. Relieve pressure and disconnect precolumn carefully. With small spatula remove a few mm (2–4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

EXAMPLE 6

The following procedure, which gives the preparation of the compound of formula 3 wherein $R^1$ is $CH_3(CH_2)_{11}$—, illustrates preparation of the compounds of formula 3, using the "active ester" method.

n-Tridecanoyl Derivative of S 31794/F-1 Nucleus

A. Preparation of 2,4,5-Trichlorophenyl n-Tridecanoate.

A solution of n-tridecanoic acid (Sigma Chemical Co.) (12.5 g), 2,4,5-trichlorophenol (11.5 g), and N,N'-dicyclohexylcarbodiimide (12.0 g) in methylene chloride (650 ml) is stirred at room temperature for 16 hours. The reaction mixture is then filtered and dried in vacuo to give 2,4,5-trichlorophenyl n-tridecanoate (22 g). The material is purified by column chromatography over silica gel (Woelm) using toluene as the eluent. Fractions are monitored by TLC using a shortwave UV light for detection. Fractions containing the purified product are pooled and concentrated in vacuo to dryness.

B. Acylation of S 31794/F-1 Nucleus with 2,4,5-Trichlorophenyl n-Tridecanoate.

A solution of 2,4,5-trichlorophenyl n-tridecanoate (3.3 mmoles) and S 31794/F-1 nucleus (1 mmole) in dimethylformamide (DMF) (200 ml) is stirred at room temperature for 16 hours. Removal of solvent in vacuo affords a residue. The residue is slurried with methylene chloride (300 ml) for 45 minutes, and the mixture is filtered. The filtrate is discarded. The remaining solids are extracted with methanol (300 ml), and the methanol extract is filtered and concentrated in vacuo to give a crude product.

The crude product is purified by reversed-phase HPLC as follows:

A sample of the crude product (1 g), dissolved in methanol (5 ml), is injected into a 1-×32-inch stainless steel column packed with LP-1/$C_{18}$ resin (see Example 4). The column is eluted with a solvent system comprising 3:3:4 $H_2O/CH_3OH/CH_3CN$. The elution is performed at a pressure of 1000-1500 psi with a flow rate of 11-12 ml/min using an LDC duplex pump (Milton-Roy). The effuent is monitered by a UV detector (ISCO-UA-5) at 280 nm. Fractions are collected every two minutes (21-24 ml). The fractions containing the desired product are pooled and dried in vacuo to afford the title product. The purified product is analyzed by TLC using reversed-phase $C_{18}$ plates (Whatman $KC_{18}$) and a solvent system comprising 1:2:2 (v/v) $H_2O/CH_3OH/CH_3CN$. After development, the plates are observed under UV light to detect the product.

EXAMPLE 7

The following procedure, which gives the preparation of the compound of formula 4 wherein $R^1$ is N-(n-dodecanoyl)-p-aminobenzoyl, illustrates the method of preparation of the Debono I compounds of formula 4.

N-(n-Dodecanoyl)-p-aminobenzoyl Derivative of S 31794/F-1 Nucleus

A. Preparation of N-(n-Dodecanoyl)-p-aminobenzoic Acid n-Dodecanoyl chloride (8.74 g; 40 mmoles) is added dropwise to a solution of p-aminobenzoic acid (40 mmoles) dissolved in pyridine (100 ml). The mixture is stirred for 3 hours and poured into water (3 L). The precipitate which forms is filtered and dried in vacuo to give N-(n-dodecanoyl)-p-aminobenzoic acid (11.01 g).

B. Preparation of the 2,4,5-Trichlorophenyl Ester of N-(n-Dodecanoyl)-p-aminobenzoic Acid N-(n-Dodecanoyl)-p-aminobenzoic acid (11.01 g; 34.5 mmoles), 2,4,5-trichlorophenol (7.5 g; 38 mmoles), and N,N'-dicyclohexylcarbodiimide (6.94 g; 34.5 mmoles) are dissolved in methylene chloride (250 ml). The mixture is stirred at room temperature for 3.5 hours and then filtered. The filtrate is evaporated in vacuo to give a residue which is crystallized from acetonitrile/water to afford the 2,4,5-trichlorophenyl ester of N-(n-dodecanoyl)-p-aminobenzoic acid (12.84 g).

C. Acylation of S 31794/F-1 Nucleus

S 31794/F-1 nucleus (10.2 mmoles) and the 2,4,5-trichlorophenyl ester of N-(n-dodecanoyl)-p-aminobenzoic acid (10.2 mmoles) are dissolved in dimethylformamide (100 ml). The solution is stirred at room temperature for 15 hours. Solvent is removed in vacuo to give a residue which is washed twice with diethyl ether. The washes are discarded. The washed residue is dissolved in methanol (50 ml) and is purified by reversed phase HPLC by means of a "Prep LC/System 500" unit (Waters Associates, Inc., Milford, Mass.) using a Prep Pak-500/C18 column (Water Associates, Inc.) as the stationary phase. The column is eluted isocratically with $H_2O/CH_3OH/CH_3CN$ (25:65:10 v/v) at 500 psi. The fractions are analyzed by TLC using silica gel plates and $H_2O/CH_3OH/CH_3CN$ (25:65:10 v/v) as the solvent system. Fractions containing the desired product are combined and lyophilized to give the N-(n-dodecanoyl)-p-aminobenzoyl derivative of S 31794/F-1 nucleus.

EXAMPLE 8

The following procedure, which gives the preparation of the compound of formula 4 wherein $R^1$ is p-(n-octyloxy)benzoyl illustrates the method of preparation of the Debono II compounds of formula 4.

p-(n-Octyloxy)benzoyl Derivative of S 31794/F-1 Nucleus

A. Preparation of p-(n-Octyloxy)benzoic Acid

A solution of p-hydroxybenzoic acid (19.2 g, 150 moles) in 10% aqueous sodium hydroxide (120 ml) is added to dimethyl sulfoxide (DMSO) (480 ml) previously heated to 80° C. n-Octyl bromide (28.95 g, 150 moles) is added dropwise to the solution. The reaction mixture is stirred for 4 hours at room temperature after which it is poured into ice water (1200 ml). Conc. hydrochloric acid (30 ml) is added, and the mixture is allowed to stand until precipitation is complete. The precipitate is collected, dried, and crystallized from acetonitrile-water. mp 97°-99° C.

Analysis for $C_{15}H_{22}O_3$: Calculated: C, 71.97; H, 8.86; Found: C, 71.72, H, 9.10.

B. Preparation of the 2,4,5-Trichlorophenyl Ester of p-(n-Octyloxy)benzoic Acid p-(n-Octyloxy)benzoic acid (6.18 g, 24.7 mmoles), 2,4,5-trichlorophenol (5.39 g, 27.2 mmoles) and N,N'-dicyclohexylcarbodiimide (4.94 g, 24.7 mmoles) are dissolved in methylene chloride (200 ml). The mixture is stirred at room temperature for 18 hours and then is filtered. The filtrate is evaporated to give an oil, which is crystallized from $CH_3CN-H_2O$ to give the 2,4,5-trichlorophenyl ester of p-(n-octyloxy)benzoic acid.

NMR Analysis: $\delta 4.02$ (2H, t, J=3 Hz), $\delta 7.0$ (1H, d, J=4 Hz), 7.23 (s, 1H), 7.3 (s, 1H), 8.08 (d, 1H J=4 Hz).

C. Acylation of S 31794/F-1 Nucleus

S 31794/F-1 nucleus (17.8 mmoles) and the 2,4,5-trichlorophenyl ester of p-(n-octyloxy)benzoic acid (35.7 mmoles) are dissolved in dimethylformamide (150 ml). The solution is stirred at room temperature for 16-20 hours. Solvent is removed in vacuo, and the residue is washed twice with diethyl ether and twice with methylene chloride. The washes are discarded. The washed residue is dissolved in ethyl acetate:methanol (1:3) (80 ml) and is purified by HPLC using a "Prep LC/System 500" unit, using silica gel as the stationary phase. The column is eluted stepwise with methanol:ethyl acetate (1:4 to 2:3) solvent systems. The fractions are analyzed by TLC using silica gel (Merck) and ethyl acetate:methanol (3:2 v/v) as the solvent system. Fractions devoid of S 31794/F-1 nucleus are pooled and lyophilized to give the p-(n-octyloxy)benzoyl derivative of S 31794/F-1 nucleus.

We claim:

1. S 31794/F-1 nucleus of the formula

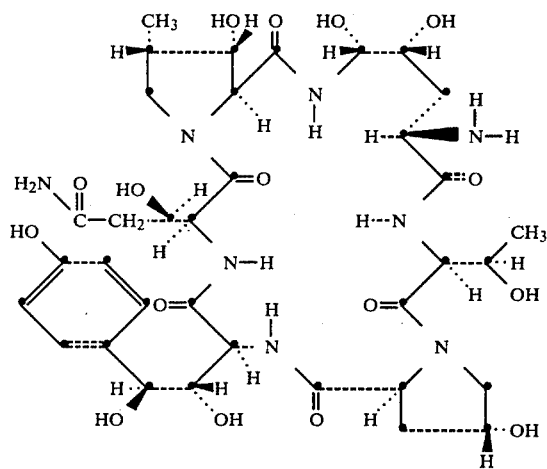

and the acid addition salts thereof.

2. The compound of claim 1 which is S 31794/F-1 nucleus.

3. The method of deacylating antibiotic S 31794/F-1 which comprises exposing the antibiotic in an aqueous medium to an enzyme which deacylates and which is produced by a microorganism of the family Actinoplanaceae until substantial deacylation is accomplished.

4. The method of claim 3 wherein the microorganism of the family Actinoplanaceae is a member of the genus Actinoplanes.

5. The method of claim 4 wherein the microorganism is *Actinoplanes utahensis.*

6. The method of claim 5 wherein the microorganism is *A. utahensis* NRRL 12052 or a mutant thereof which produces the enzyme.

7. The method of claim 6 wherein the microorganism is *A. utahensis* NRRL 12052.

8. The method of claim 3 wherein the microorganism is *Streptosporangium roseum* var. *hollandensis* NRRL 12064, or a mutant thereof which produces the enzyme.

9. The method of claim 8 wherein the microorganism is *Streptosporangium roseum* var. *hollandensis* NRRL 12064.

10. The method of claim 4 wherein the microorganism is *Actinoplanes missouriensis* NRRL 12053 or a mutant thereof which produces the enzyme.

11. The method of claim 10 wherein the microorganism is *Actinoplanes missouriensis* NRRL 12053.

12. The method of claim 4 wherein the microorganism is *Actinoplanes sp.* NRRL 12065 or a mutant thereof which produces the enzyme.

13. The method of claim 12 wherein the microorganism is *Actinoplanes sp.* NRRL 12065.

14. The method of claim 4 wherein the microorganism is *Actinoplanes sp.* NRRL 8122 or a mutant thereof which produces the enzyme.

15. The method of claim 14 wherein the microorganism is *Actinoplanes sp.* NRRL 8122.

16. A method of claims 3, 4, 5, 6, 7, 8, 9, 10, 11, 12, 13, 14, or 15 wherein the enzyme is present in a culture of the producing Actinoplanaceae microorganism.

* * * * *